(12) United States Patent
Kadobayashi et al.

(10) Patent No.: US 10,311,753 B2
(45) Date of Patent: Jun. 4, 2019

(54) COMPRESSION METHOD TOOTH

(71) Applicant: SHOFU INC., Kyoto (JP)

(72) Inventors: Yusei Kadobayashi, Kyoto (JP); Masako Shigezawa, Kyoto (JP)

(73) Assignee: SHOFU INC., Kyoto (JP)

( * ) Notice: Subject to any disclaimer, the term of this patent is extended or adjusted under 35 U.S.C. 154(b) by 362 days.

(21) Appl. No.: 15/017,873

(22) Filed: Feb. 8, 2016

(65) Prior Publication Data

US 2016/0293056 A1    Oct. 6, 2016

(30) Foreign Application Priority Data

Apr. 1, 2015  (JP) ................. 2015-074775

(51) Int. Cl.
| | | |
|---|---|---|
| *G09B 23/28* | (2006.01) | |
| *A61C 13/08* | (2006.01) | |
| *A61C 13/09* | (2006.01) | |
| *A61K 6/027* | (2006.01) | |
| *B29C 43/14* | (2006.01) | |
| *A61K 6/00* | (2006.01) | |
| *B29L 31/00* | (2006.01) | |

(52) U.S. Cl.
CPC .......... *G09B 23/283* (2013.01); *A61C 13/081* (2013.01); *A61C 13/09* (2013.01); *A61K 6/0097* (2013.01); *A61K 6/027* (2013.01); *B29C 43/146* (2013.01); *B29C 2043/147* (2013.01); *B29K 2003/00* (2013.01); *B29L 2031/7536* (2013.01)

(58) Field of Classification Search
USPC ....... 434/263; 264/16, 19; 433/201.1, 202.1, 433/212.1, 213
See application file for complete search history.

(56) References Cited

U.S. PATENT DOCUMENTS

| | | | | |
|---|---|---|---|---|
| 5,575,653 | A * | 11/1996 | Freyer ................ | A61C 13/0003 264/138 |
| 8,002,549 | B2 * | 8/2011 | Kadobayashi ....... | A61C 13/097 433/171 |
| 8,267,695 | B2 * | 9/2012 | Kadobayashi ....... | G09B 23/283 264/16 |
| 8,632,889 | B2 * | 1/2014 | Thiel .................. | A61C 13/0022 428/161 |

(Continued)

FOREIGN PATENT DOCUMENTS

| | | |
|---|---|---|
| JP | 05-216395 | 8/1993 |
| JP | 07-309972 | 11/1995 |

(Continued)

OTHER PUBLICATIONS

Notification of Reasons for Refusal dated Apr. 28, 2015 in Japanese Application No. 2015-074775, with English Translation provided by the Global Dossier.

(Continued)

*Primary Examiner* — Kurt Fernstrom

(74) *Attorney, Agent, or Firm* — Wenderoth, Lind & Ponack, L.L.P.

(57) ABSTRACT

The compression molded tooth used for practicing dental cutting treatment of the present invention comprises a composition containing a powder or powders of saccharide, polysaccharide, protein, and/or glycoprotein each having a particle size of 1 to 100 μm.

8 Claims, 6 Drawing Sheets

(56) References Cited

U.S. PATENT DOCUMENTS

| | | | |
|---|---|---|---|
| 2006/0024652 A1* | 2/2006 | Ose .................... | G09B 23/283 434/263 |
| 2009/0263774 A1* | 10/2009 | Pichardo ............. | G09B 23/283 434/263 |
| 2010/0015588 A1* | 1/2010 | Funakoshi ........... | G09B 23/283 434/263 |
| 2013/0180110 A1 | 7/2013 | Schechner et al. | |
| 2014/0024003 A1* | 1/2014 | Iwaki .................. | G09B 23/283 434/263 |
| 2014/0030685 A1 | 1/2014 | Kadobayashi et al. | |

FOREIGN PATENT DOCUMENTS

| | | |
|---|---|---|
| JP | 08-73613 | 3/1996 |
| JP | 2007-310373 | 11/2007 |
| JP | 2007-323051 | 12/2007 |

OTHER PUBLICATIONS

Extended European Search Report dated Jul. 29, 2016 in European Application No. 16154611.4.

\* cited by examiner

COMPRESSION METHOD TOOTH

BACKGROUND OF THE INVENTION

Field of the Invention

The present invention relates to a tooth for a jaw tooth model for a dental student to practice abutment tooth preparation, cavity preparation, and the like.

Description of the Related Art

Conventionally, a tooth for a jaw tooth model has been prepared from an epoxy resin or a melamine resin.

Further, a tooth material using a hydroxyapatite powder and a (meth)acrylate resin is introduced in Japanese Patent Laid Open No. 5-216395.

A tooth prepared from alumina is introduced in Japanese Patent Laid Open No. 2007-310373.

An environmentally friendly tooth material is required because bisphenol A is used in an epoxy resin and formaldehyde is used in a melamine resin.

Further, the teeth prepared from the tooth materials disclosed in Japanese Patent Laid Open No. 5-216395 and Japanese Patent Laid Open No. 2007-310373 have a problem of cutting feeling and a problem that the disposal of the teeth after cutting practice is not easy. Since the cutting waste of a tooth may be sucked by a student or scattered, a tooth made of a safe material has been required. Further, a tooth that can experience the dental pulp exposure of a natural tooth has been required.

The present invention provides a tooth for a jaw tooth model for a dental student to practice abutment tooth preparation, cavity preparation, and the like, wherein the tooth can be easily discarded after having been used for cutting practice. Further, the tooth of the present invention can provide a cutting feeling that is the same as that of a natural tooth.

According to the method for producing a tooth of the present invention, the tooth of the present invention can be easily produced without polymerizing a resin and without firing a material.

SUMMARY OF THE INVENTION

A compression molded tooth used for practicing dental cutting treatment of the present invention comprises a composition containing a saccharide powder, a polysaccharide powder, a protein powder, and/or a glycoprotein powder each having a particle size of 1 to 100 μm, and is obtained by compression molding. The compression molded tooth contains the saccharide, polysaccharide, protein, and/or glycoprotein in an amount of 10 to 100% by mass, preferably 70 to 100% by mass.

The compression molding can be performed in a plurality of steps in order to mold the tooth uniformly, and in this case, the tooth will have portions where the numbers of compression molding cycles are different. If the compression molded tooth is molded at one time, variations in compression may occur in the tooth to cause poor molding.

The compression molded tooth may comprise a first portion constituting an enamel tooth portion and a second portion constituting a dentin tooth portion. In this case, as a procedure of compression molding, the enamel tooth portion may be molded first, and the dentin tooth portion may be molded later. In the compression molded tooth molded in this way, the number of compression molding cycles for the first portion is larger than the number of compression molding cycles for the second portion. It is necessary to accurately mold the shape of a crown in the enamel tooth portion as compared with the dentin tooth portion. The crown shape can be accurately molded by molding a crown contour first and then molding the dentin tooth portion gradually. Further, the cutting resistance of the tooth can be improved by increasing molding pressure, and the tooth can be soft by decreasing molding pressure. Therefore, molding pressure is increased for the enamel tooth portion, and the molding pressure is gradually decreased as the dentin tooth portion is molded, thereby capable of gradually preparing a tooth having portions different in cuttability.

However, since the cuttability of the enamel tooth portion is largely different from that of the dentin tooth portion, it is preferred in the molding to largely change the molding pressure at the enamel-dentin junction.

The compression molded tooth preferably has a third portion different from the first portion and the second portion therein. Specifically, the third portion constitutes a dental caries portion, a dental pulp portion, and/or a cutting target portion. The dental caries portion refers to a false dental caries portion provided on or inside an occlusal surface. The dental pulp portion refers to a false dental pulp provided in the vicinity of the central part of a tooth. The cutting target portion is provided in the abutment tooth or cavity.

The third portion may also be prepared from a component different from that of the first portion and the second portion such as a resin and silicone, may also be molded by compressing a saccharide powder or a polysaccharide powder, and is preferably subjected to preliminary compression molding.

Next, a method for producing a compression molded tooth of the present invention will be described.

In the method for producing a compression molded tooth of the present invention, a crown side can be molded using a concave mold, and a root side can be molded using a convex mold.

Specifically, an enamel tooth portion closer to an occlusal surface can be molded using a first convex mold, and then a dentin tooth portion can be molded using a second convex mold. Further, it is possible to mold several times before molding using the first convex mold. Similarly, it is possible to mold several times before molding using the second convex mold. By molding repeatedly, variations in compression are eliminated, and variations in cutting resistance are reduced.

Molding pressure for the first convex mold is 20 to 100 MPa; molding pressure for the second convex mold is 5 to 85 MPa; and the molding pressure for the second convex mold is lower by 15 MPa or more as compared with the molding pressure for the first convex mold. The enamel tooth portion, which is molded using the first convex mold, preferably has higher cutting resistance than the dentin tooth portion molded using the second convex mold. In some cases, cuttability can be changed by gradually changing molding pressure or by gradually increasing the amount of molding.

The present invention can provide a tooth for a jaw tooth model for a dental student to practice abutment tooth preparation, cavity preparation, and the like, wherein the tooth can be easily discarded after having been used for cutting practice. Further, the present invention can provide a tooth that can obtain a cutting feeling that is the same as that of a natural tooth.

According to the method for producing a tooth of the present invention, the tooth of the present invention can be easily produced without polymerizing a resin and without firing a material.

DETAILED DESCRIPTION OF THE PREFERRED EMBODIMENTS

Figure 1:
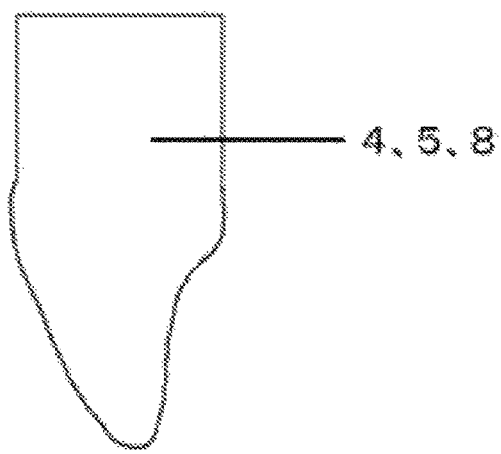
FIG. 1 is a view of tooth morphology obtained by powder compression molding in a single layer.

A compression molded tooth used for practicing dental cutting treatment of the present invention comprises a composition containing a powder or powders of saccharide, polysaccharide, protein, and/or glycoprotein each having a particle size of 1 to 100 μm.

Examples of the saccharide, polysaccharide, protein, and glycoprotein are as shown below.

Examples of monosaccharides include trioses "ketotriose (dihydroxyacetone) and aldotriose (glyceraldehyde)", tetroses "ketotetrose (erythrulose) and aldotetrose (erythrose and threose)", pentoses "ketopentose (ribulose and xylulose), aldopentose (ribose, arabinose, xylose, and lyxose), and deoxy sugars (deoxyribose)", hexoses "ketohexoses (psicose, fructose, sorbose, and tagatose), aldohexoses (allose, altrose, glucose, mannose, gulose, idose, galactose, and talose), and deoxy sugars (fucose, fuculose, and rhamnose)", and heptoses "sedoheptulose".

Examples of polysaccharides include disaccharides "sucrose, lactose, maltose, trehalose, turanose, and cellobiose", trisaccharides "raffinose, melezitose, and maltotriose", tetrasaccharides "acarbose and stachyose", other oligosaccharides "fructo-oligosaccharide (FOS), galacto-oligosaccharide (GOS), and mannan-oligosaccharide (MOS)", polysaccharides "glucose: glycogen, starch (amylose and amylopectin), cellulose, dextrin, glucan (β-1,3-glucan), fructose: fructan (inulin and levan β-2→6), and N-acetyl glucosamine: chitinous substance", oligosaccharides "fructo-oligosaccharide, "galacto-oligosaccharide, and lactosucrose", deoxy sugars "deoxyribose, fucose, rhamnose", uronic acid "glucuronic acid and galacturonic acid", amino sugar "glucosamine and galactosamine", sugar alcohol "glycerin, xylitol, and sorbitol", lactone "ascorbic acid (vitamin C), glucuronolactone, and gluconolactone", and polysaccharides "starch, amylose, amylopectin, glycogen, cellulose, pectin, and glucomannan".

A polymer compound in which a large number of L-amino acids, which are present in 20 types, are linked together (polymerized) in a chain may be used as a protein, and specifically, it is preferred to use powdered milk. The milk powder can be obtained directly from milk as a white product. Therefore, when the milk powder is used as a tooth material, it is not necessary to pass through steps such as extraction and coloration. Further, since it has not passed through steps such as extraction and coloration, it is possible to directly utilize the tooth material as a livestock food after use. Further, this is because, when preparing a compression molded tooth, steps other than compression molding are not required, and the hardness of the compression molded tooth can be changed only by adjusting compression pressure.

A compound in which a sugar chain is combined with a part of an amino acid constituting a protein can be used as a glycoprotein, and specific examples include glucose, galactose, mannose, fucose, N-acetyl glucosamine, N-acetyl galactosamine, N-acetyl neuraminic acid, and xylose.

Preferred saccharides, polysaccharides, proteins, and/or glycoproteins are sugar alcohol, a polysaccharide, and a protein. Specific examples of sugar alcohol include erythritol, glycerin, HSH, isomalt, lactitol, maltitol, mannitol, sorbitol, xylitol, and sucrose. Specific examples of polysaccharides include starch (amylose and amylopectin), glycogen, cellulose, chitin, agarose, carrageenan, heparin, hyaluronic acid, pectin, and xyloglucan. Specific examples of proteins include powdered milk. Among these, more preferred examples of sugar alcohol include maltitol, sorbitol, and xylitol; more preferred examples of polysaccharides include starch (amylose and amylopectin), glycogen, and cellulose; and more preferred examples of proteins include powdered milk.

The compression molded tooth preferably contains a saccharide, a polysaccharide, a protein, and/or a glycoprotein in an amount of 10% by mass or more, more preferably 70% by mass or more, further preferably 98% by mass or more, and most preferably about 100% by mass except for a colorant and the like.

The saccharide powder, polysaccharide powder, protein powder, and/or glycoprotein powder is a powder having an average particle size of 1 to 100 μm, preferably 10 to 70 μm. In this application, the average particle size may be measured according to ISO 13322-1.

The compression molded tooth may contain other powders such as a powder of inorganic materials and/or organic materials other than the saccharide powder, polysaccharide powder, protein powder, and/or glycoprotein powder. In this case, the saccharide powder, polysaccharide powder, protein powder, and/or glycoprotein powder acts also as a binder to bond other powders.

The powder of inorganic materials may be a powder, for example, typified by glass powder, ceramic powder, and the like. The powder of organic materials may be, for example, a resin powder. The powder of these inorganic materials and/or organic materials preferably has an average particle size of 0.1 to 30 μm, preferably 1 to 15 μm.

A dye and/or a pigment is preferably added to these materials as a colorant to thereby color these materials in tooth color such as ivory color.

Compression molding is a technique of compressing a material to thereby mold the same. In the present invention, the compression molding specifically includes preparing a negative mold of a target shape as a mold, filling the negative mold with a predetermined powder material, and applying pressure to the powder material from a predetermined direction to thereby mold the powder material. Further, after applying a predetermined pressure, the negative mold is further filled with a powder material, and pressure is applied to the powder material from a predetermined direction, thereby capable of molding the powder in layers.

Variations in cuttability caused by variations in compression can be reduced by repeating molding. If a thick molded article is prepared by one-time compression molding without dividing the compression molding into a plurality of number of times, variations in compression may occur. It is preferred to mold a molded article having a thickness of 2 to 5 mm. Only the crown portion in which an abutment tooth and a cavity are formed is a portion in which such variations in cuttability must be removed. Since it is Satis-factory even if a root portion has variations in cuttability, one-time molding can be adopted.

As a procedure of compression molding, it is preferred to mold the first portion constituting the enamel tooth portion first and mold the second portion constituting the dentin tooth portion later. It is preferred to mold the crown contour of the enamel tooth portion and then advance the molding toward the dentin and root side.

The compression molded tooth preferably has a third portion which is different from the first portion constituting the enamel tooth portion and the second portion constituting the dentin tooth portion.

The third portion may be a portion that constitutes a dental caries portion, a dental pulp portion, and/or a cutting target portion, and when the third portion constitutes any of these portions, it can be prepared in the same manner.

The third portion can be prepared by a method in which materials colored with a colorant are laminated to prepare a layered material for the third portion, and when a compression molded tooth is molded, the layered material is contained inside the tooth. (First preparation method) The materials can be colored with a dye, a pigment, a fluorescent material, and the like.

The third portion can also be prepared by a method in which the layered material for the third portion described above is preliminarily molded to prepare a preliminarily-molded layered member for the third portion, and when the compression molded tooth is molded, the preliminarily-molded layered member for the third portion is contained inside the tooth. (Second preparation method)

Alternatively, the third portion can also be prepared by a method in which a resin layer member for the third portion is prepared beforehand from a resin, and when the compression molded tooth is molded, the resin layer member for the third portion is contained inside the tooth. A silicone resin and an organic polymer can be used as the resin. (Third preparation method)

A preferred method when the third portion constitutes a dental caries portion or a cutting target portion is the first preparation method and the second preparation method. Cuttability can be varied closer to the cuttability of a natural tooth by changing the composition and the like.

A preferred method when the third portion constitutes a dental pulp portion is the third preparation method. The feeling of the dental pulp exposure becomes close to the cuttability of a natural tooth by preparing the pulp from a resin.

Dental college students use a tooth for a jaw tooth model for the practice of abutment tooth preparation and cavity preparation. The technique cannot be mastered by several times of practice, but many teeth are consumed for mastering the technique. Since a tooth made of a resin has been mainly used, incineration or the like has been a main method for waste disposal, which is not environmentally friendly. Since saccharides, polysaccharides, proteins, and/or glycoproteins are used in the present invention, the waste can be used as animal feed or can undergo microbial degradation, which is environmentally friendly.

Further, since the molding method of a tooth is compression molding, the consumption of energy is small in production, and the tooth can be easily produced in simple facilities. Furthermore, cutting feeling can be changed in a tooth, and since cutting feeling is closer to that of a natural tooth than before, the practice close to treatment can be performed.

Since dental college students perform cutting operation, dust is scattered and often sucked by the students. Therefore, it has been required to prepare a tooth from a safer material. In the present invention, a tooth can be prepared from saccharides and polysaccharide, and a safer tooth can be supplied.

Further, in the abutment tooth preparation and cavity preparation in dental treatment, the preparation must be performed so that the dental pulp exposure may not occur during the formation, but such a feeling has not been able to be experienced by a conventional tooth for a jaw tooth model. In the present invention, since the portion of a dental pulp can be formed in the tooth, it is possible to tell the dental pulp exposure.

Further, in the present invention, since not only the dental pulp but also the dental caries can be formed, experience of dental treatment in more accordance with reality can be experienced by the tooth for a jaw tooth model of the present invention.

Furthermore, initial practice does not show how much cutting should be performed for abutment tooth preparation and cavity preparation. In the present invention, a mark of how much cutting should be performed can be put on a target portion, and practice can be performed while checking the progress of cutting.

When an artificial tooth having a hard outside and soft inside is required, the artificial tooth can be prepared by one-time molding according to "Method for Preparing Artificial Tooth 1-1" to be described below. The portion of the tooth in the vicinity of a molding die is hard. Further, when an artificial tooth having a uniform cutting feeling through the inner part is required, it can be achieved by successive lamination to a thickness from 1 to 2 mm according to "Method for Preparing Artificial Tooth 1-2" to be described below.

EXAMPLES

Hereinafter, the present invention will be described with reference to Examples. However, the present invention is not limited to Examples. First, a specific method for preparing a compression molded tooth in Examples will be described.
(Formulation of Composition)

The details such as components used in Examples are as follows.
Xylitol: manufactured by NICHIGA, powder, 100 μm
Maltitol: manufactured by NICHIGA, powder, 70 μm
Starch: manufactured by Nisshin Flour Milling Company, flour (weak flour), 10 μm
Powdered milk: manufactured by Meiji Dairies Corporation, powdered skim milk, 30 μm
Silica powder (5 μm): manufactured by Tokuyama Corporation, silica powder
Carbon black: manufactured by Mitsubishi Chemical Corporation, high-class color (HCF) #2650
Red pigment (iron red): manufactured by MORISHITA BENGARA KOGYO CO., LTD., (10 μm)
Fluorescent material: fluorescent pigment (LUMILUX C-Pigments is an ultraviolet (UV) excitation type organic/inorganic fluorescent pigment)

Resin in dental pulp composition: manufactured by SHOFU, INC., Color Toning Wax Red (formed into a dental pulp shape beforehand)

Silicone in dental pulp composition: manufactured by SHOFU, INC., Lab Silicone, colored to red with iron red (formed into a dental pulp shape beforehand).

These components were mixed in composition ratios (mass ratio) shown in Table 1 to obtain composition raw materials each having a composition name shown in Table 1.

Next, the composition raw materials each having a composition name shown in Table 1 were used to prepare artificial teeth shown in Table 2. The preparation method is shown below.

(Method for Preparing Artificial Tooth 1-1)

A method for preparing an artificial tooth shown in FIG. 1 will be described. FIG. 1 is a view of an artificial tooth in which an enamel tooth portion 4, a dentin tooth portion 5, and a root tooth portion 8 in the artificial tooth were molded from the same composition raw material at the same time.

Figure 2:
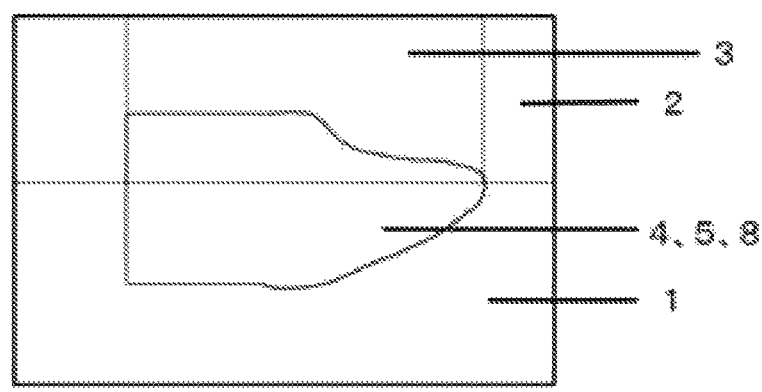
FIG. 2 is a production conceptual diagram of a tooth and a mold under powder compression molding in a single layer.

The artificial tooth of FIG. 1 is prepared using the mold shown in FIG. 2.

A method for preparing the mold of FIG. 2 and a method for preparing an artificial tooth using the mold of FIG. 2 will be described below.

Step 1: A bottom mold 1 of a concave mold which is a split mold divided at the widest contour portion with the labial surface of the artificial tooth facing downward is prepared. The bottom mold 1 of the concave mold is preferably provided with a pushing structure for removing the artificial tooth.

Step 2: Next, a side mold 2 of the concave mold is set as a sheath in which a composition raw material is put and as a receiver of a pressing mold. The side mold 2 of the concave mold is preferably prepared such that the side mold is formed along the widest contour portion of the bottom mold 1 of the concave mold; the side mold is provided with a taper of 1 to 10°; and as a result, the pressing mold can be easily inserted.

Step 3: Next, a convex mold 3 is prepared along the side mold 2 of the concave mold. The convex mold 3 is prepared so that a space for an artificial tooth may be formed when the convex mold is combined with the bottom mold 1 of the concave mold.

Step 4: The side mold 2 of the concave mold is set to the bottom mold 1 of the concave mold; a predetermined amount of a composition raw material is charged into a recess; and the convex mold 3 is inserted into the recess so that the composition raw material may be sandwiched. The composition raw material was compression molded by pressurizing (molding pressure is described in Table 2) with a compressor to obtain the artificial tooth.

(Method for Preparing Artificial Tooth 1-2)

Further, another method for preparing an artificial tooth will be described below.

In order to mold an artificial tooth for each layer having a thickness of 1 to 2 mm, a plurality of convex molds 3 are prepared in Step 3 of the above "(Method for Preparing Artificial Tooth 1-1)". A composition raw material was filled for each layer and successively pressurized with a compressor using the plurality of convex molds 3 (molding pressure is described in Table 2) to thereby obtain the artificial tooth.

Figure 3:
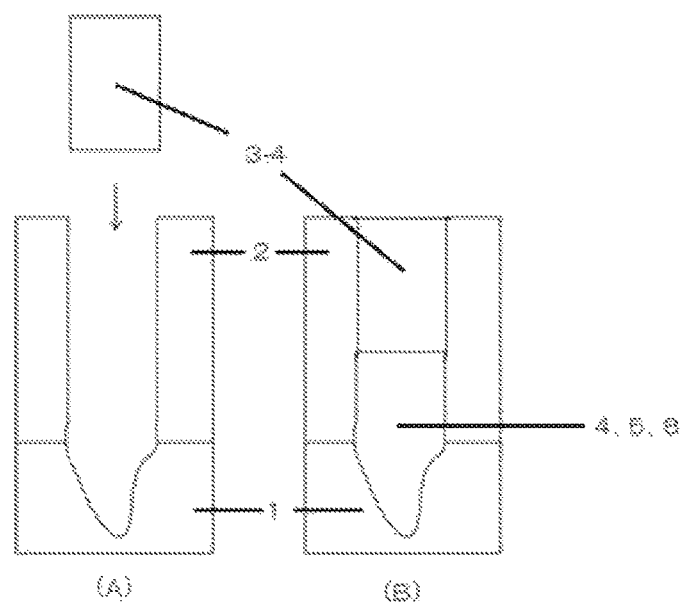
FIG. 3 is a production conceptual diagram of a tooth and a mold under powder compression molding in a single layer.

An artificial tooth can be molded in the same manner also from the direction shown in FIG. 3. However, since the molding direction is changed, the contour of the bottom mold 1 of the concave mold and the side mold 2 of the concave mold are changed, and the convex mold 3 is a fourth convex mold 3-4. FIG. 3 (A) is a conceptual diagram in which the side mold 2 of the concave mold is set to the bottom mold 1 of the concave mold before inserting the convex mold 3 (fourth convex mold 3-4), and FIG. 3 (B) is a conceptual diagram in which the convex mold 3 (fourth convex mold 3-4) of FIG. 3 (A) is inserted.

An artificial tooth molded from the same composition raw material is more preferably molded by a method of molding an artificial tooth from the molding direction of FIG. 2 as compared with a method of molding an artificial tooth from the molding direction of FIG. 3. Pressure is uniformly applied to the whole artificial tooth to provide better moldability.

Ten artificial teeth were respectively molded from the compositions and under the molding conditions shown in Examples 1 to 10 using the molds of FIG. 2 and FIG. 3 by the above two types of methods "(Method for Preparing Artificial Tooth 1-1)" and "(Method for Preparing Artificial Tooth 1-2). It was verified that the artificial teeth could be molded satisfactorily. Each composition raw material and molding condition are described in Table 2.

(Method for Preparing Artificial Tooth 2-1)

Figure 4:
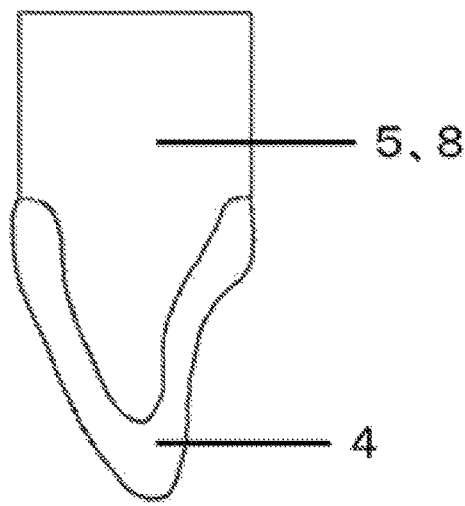
FIG. 4 is a view of tooth morphology obtained by powder compression molding in two layers of an enamel tooth and a dentin tooth.

The method for preparing an artificial tooth shown in FIG. 4 will be described. FIG. 4 is a view of an artificial tooth in which the dentin tooth portion 5 and the root tooth portion 8 were molded from the same composition raw material and under the same molding conditions, and the enamel tooth portion 4 was molded from a different composition raw material and/or under different molding conditions, in the artificial tooth.

This is a method for preparing an artificial tooth for reproducing a change of the cutting feeling, particularly, in the case of moving from the enamel tooth portion to the dentin tooth portion, for the purpose of obtaining a cutting feeling of the enamel tooth portion and a cutting feeling of the dentin tooth portion, respectively.

Figure 5:
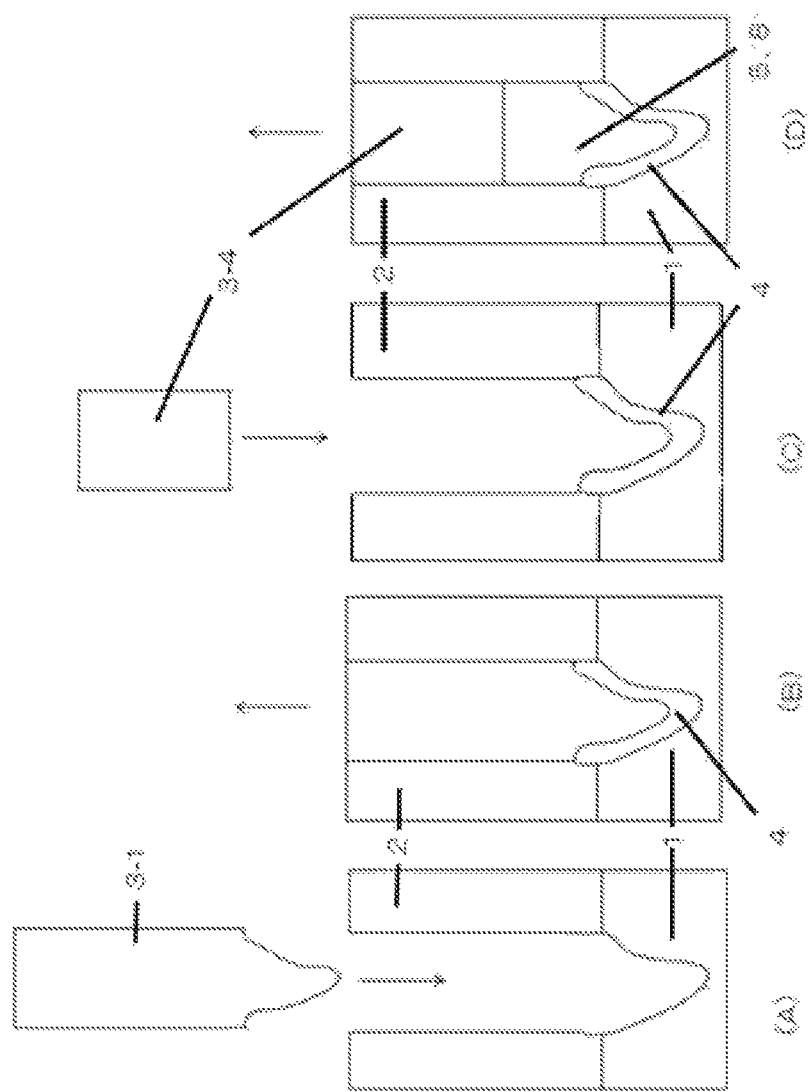
FIG. 5 is a production conceptual diagram of a tooth and a mold under powder compression molding in two layers of an enamel tooth and a dentin tooth.

The artificial tooth of FIG. 4 is prepared using the mold shown in FIG. 5.

A method for preparing the mold of FIG. 4 and a method for preparing an artificial tooth using the mold of FIG. 4 will be described below.

Step 1: A bottom mold 1 of a concave mold which is a split mold divided at the widest contour portion with the occlusal surface of the artificial tooth facing downward is prepared. The bottom mold 1 of the concave mold is preferably provided with a pushing structure for removing the artificial tooth.

Step 2: A side mold 2 of the concave mold is set as a sheath in which a composition raw material is put and as a receiver of a pressing mold. The side mold 2 of the concave mold is preferably prepared such that the side mold is formed along the widest contour portion of the bottom mold 1 of the concave mold; the side mold is provided with a taper of 1 to 10°; and as a result, the pressing mold can be easily inserted.

Step 3: A convex mold 3 (third convex mold 3-1) for molding the enamel tooth portion is prepared. The third convex mold 3-1 is prepared along the side mold 2 of the concave mold so that a space for the enamel tooth portion may be formed when the convex mold is combined with the bottom mold 1 and the side mold 2 of the concave mold (FIG. 5 (B)).

Step 4: A fourth convex mold 3-4 for molding the dentin tooth portion 5 and the root tooth portion 8 is prepared. The fourth convex mold 3-4 is prepared along the side mold 2 of the concave mold so that a space for the artificial tooth may be formed when the convex mold is combined with the bottom mold 1 and the side mold 2 of the concave mold (FIG. 5 (D)).

Step 5: The side mold 2 of the concave mold is set to the bottom mold 1 of the concave mold (FIG. 5 (A)); a predetermined amount of a composition raw material suitable for the enamel tooth portion is charged into a recess; and the first convex mold 3-1 is inserted into the recess so that the composition raw material may be sandwiched (FIG. 5 (A) and (B)). The composition raw material was compression molded by pressurizing (molding pressure is described in Table 2) with a compressor to obtain the enamel tooth portion.

Step 6: A predetermined amount of a composition raw material suitable for the dentin tooth portion and the root tooth portion is charged into a recess; and the fourth convex mold 3-4 is inserted into the recess so that the composition raw material may be sandwiched (FIG. 5 (C) and (D)). The composition raw material was compression molded by pressurizing (molding pressure is described in Table 2) with a compressor to obtain the artificial tooth.

(Method for Preparing Artificial Tooth 2-2)

Further, another method for preparing an artificial tooth will be described below.

In order to mold an artificial tooth for each layer having a thickness of 1 to 2 mm, a plurality of convex molds 3 are prepared in Steps 3 and 4 of the above "(Method for Preparing Artificial Tooth 2-1)". A composition raw material was filled for each layer and successively pressurized with a compressor using the plurality of convex molds 3 (molding pressure is described in Table 2) to thereby obtain the artificial tooth.

Ten artificial teeth were respectively molded from the compositions and under the molding conditions shown in Examples 11 to 19 using the mold of FIG. 5 by the above two types of methods "(Method for Preparing Artificial Tooth 2-1)" and "(Method for Preparing Artificial Tooth 2-2). It was verified that the artificial teeth could be molded satisfactorily. Each composition raw material and molding condition are described in Table 2.

(Method for Preparing Artificial Tooth 3-1)

Figure 6:
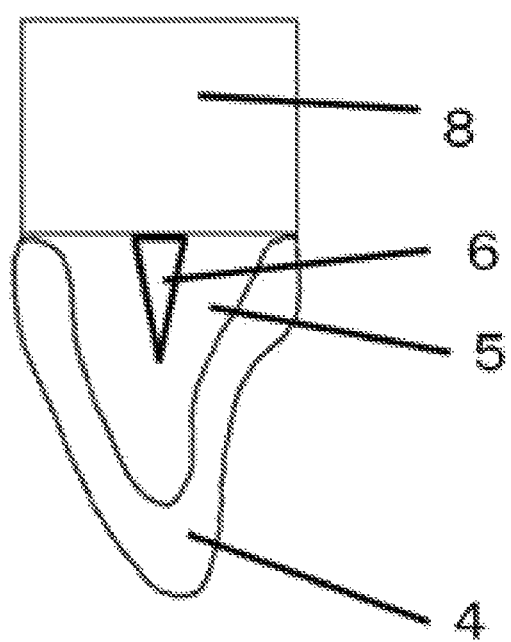
FIG. 6 is a view of tooth morphology obtained by powder compression molding in three layers of an enamel tooth, a dentin tooth, and a dental pulp (third layer)

The method for preparing an artificial tooth shown in FIG. 6 will be described. FIG. 6 is a view of an artificial tooth in which the enamel tooth portion 4, the dentin tooth portion 5, the root tooth portion 8, and a third portion (layer (dental pulp)) 6 in the artificial tooth were respectively prepared from the same or different composition raw material and/or under different molding conditions.

This is a method for preparing an artificial tooth for the purpose of obtaining a cutting feeling of the enamel tooth portion and a cutting feeling of the dentin tooth portion, respectively, and further for the purpose of reproducing a change of the cutting feeling in the case of moving from the dentin tooth portion to the layer of the third portion, the dental pulp 6.

Figure 7:
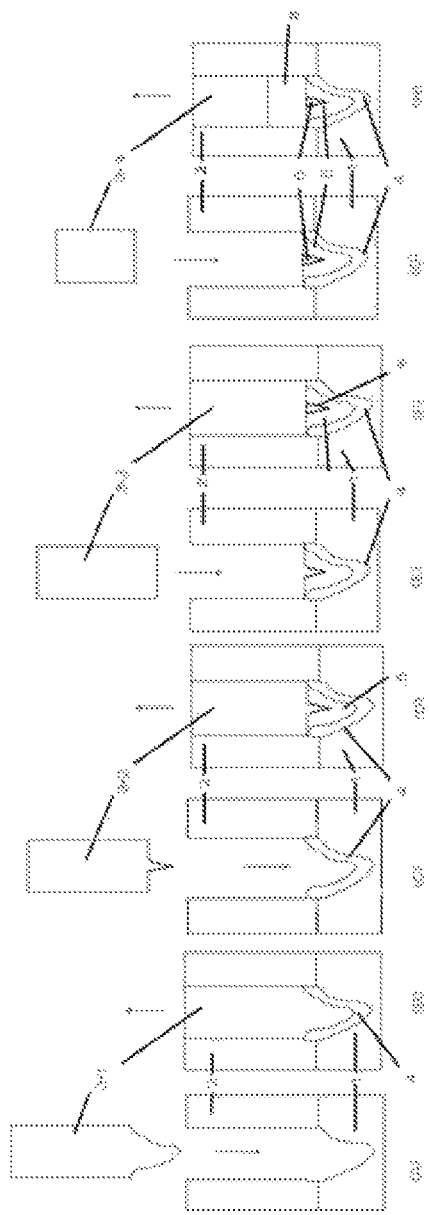
FIG. 7 is a production conceptual diagram of a tooth and a mold under powder compression molding in three layers of an enamel tooth, a dentin tooth, and a dental pulp (third layer)

The artificial tooth of FIG. 6 is prepared using the mold shown in FIG. 7.

A method for preparing the mold of FIG. 7 and a method for preparing an artificial tooth using the mold of FIG. 7 will be described below.

Step 1: A bottom mold 1 of a concave mold which is a split mold divided at the widest contour portion with the occlusal surface of the artificial tooth facing downward is prepared. The bottom mold 1 of the concave mold is preferably provided with a pushing structure for removing the artificial tooth.

Step 2: A side mold 2 of the concave mold is set as a sheath in which a composition raw material is put and as a receiver of a pressing mold (FIG. 7 (A)). The side mold 2 of the concave mold is preferably prepared such that the side mold is formed along the widest contour portion of the bottom mold 1 of the concave mold; the side mold is provided with a taper of 1 to 10°; and as a result, the pressing mold can be easily inserted.

Step 3: A convex mold 1 (first convex mold 3-1) for molding the enamel tooth portion 4 is prepared. The first convex mold 3-1 is prepared along the side mold 2 of the concave mold so that a space for the enamel tooth portion may be formed when the convex mold is combined with the bottom mold 1 and the side mold 2 of the concave mold (FIG. 7 (B)).

Step 4: A convex mold 3 (second convex mold 3-2) for molding the dentin tooth portion 5 is prepared. The second convex mold 3-2 is prepared along the side mold 2 of the concave mold so that a space for the dentin tooth portion may be formed when the convex mold is combined with the bottom mold 1 and the side mold 2 of the concave mold (FIG. 7 (D)).

Step 5: A convex mold 3 (third convex mold 3-3) for molding the dental pulp portion 6 is prepared. The third convex mold 3-3 is prepared along the side mold 2 of the concave mold so that a space for the dental pulp portion 6 may be formed when the convex mold is combined with the bottom mold 1 and the side mold 2 of the concave mold (FIG. 7 (F)).

Step 6: A convex mold 3 (fourth convex mold 3-4) for molding the root tooth portion 8 is prepared. The fourth convex mold 3-4 is prepared along the side mold 2 of the concave mold so that a space for the artificial tooth may be formed when the convex mold is combined with the bottom mold 1 and the side mold 2 of the concave mold (FIG. 7 (H)).

Step 7: The side mold 2 of the concave mold is set to the bottom mold 1 of the concave mold (FIG. 7 (A)); a predetermined amount of a composition raw material suitable for the enamel portion is charged into a recess; and the first convex mold 3-1 is inserted into the recess so that the composition raw material may be sandwiched (FIG. 7 (A) and (B)). The composition raw material was compression molded by pressurizing (molding pressure is described in Table 2) with a compressor to obtain the enamel tooth portion.

Step 8: A predetermined amount of a composition raw material suitable for the dentin portion is charged into a recess, and the second convex mold 3-2 is inserted into the recess so that the composition raw material may be sandwiched (FIG. 7 (C) and (D)). The composition raw material was compression molded by pressurizing (molding pressure is described in Table 2) with a compressor to obtain the dentin tooth portion.

Step 9: A predetermined amount of a composition raw material suitable for the dental pulp portion is charged into a recess, and the third convex mold 3-3 is inserted into the recess so that the composition raw material may be sandwiched (FIG. 7 (E) and (F)). The composition raw material was compression molded by pressurizing (molding pressure is described in Table 2) with a compressor to obtain the dental pulp portion 6.

Step 10: A predetermined amount of a composition raw material suitable for the root portion is charged into a recess, and the fourth convex mold 3-4 is inserted into the recess so that the composition raw material may be sandwiched (FIG. 7 (G) and (H)). The composition raw material was compression molded by pressurizing (molding pressure is described in Table 2) with a compressor to obtain the artificial tooth.

Although a composition raw material suitable for the dental pulp portion is charged in Step 9, it is possible to produce an artificial tooth by inserting a member, which has been preliminarily molded to a dental pulp shape, into the dental pulp portion. A preliminarily molded member made of an acrylic resin and a preliminarily molded member made of silicone were used in Example 30 and Example 31, respectively.

(Method for Preparing Artificial Tooth 3-2)

Further, another method for preparing an artificial tooth will be described below.

In order to mold an artificial tooth for each layer having a thickness of 1 to 2 mm, a plurality of convex molds 3 are prepared in Steps 3, 4, 5, and 6 of the above "(Method for Preparing Artificial Tooth 3-1)". A composition raw material was filled for each layer and successively pressurized with a compressor using the plurality of convex molds 3 (molding pressure is described in Table 2) to thereby obtain the artificial tooth.

Ten artificial teeth were respectively molded from the compositions and under the molding conditions shown in Examples 20 to 31 using the mold of FIG. 7 by the above two types of methods "(Method for Preparing Artificial Tooth 3-1)" and "(Method for Preparing Artificial Tooth 3-2). It was verified that the artificial teeth could be molded satisfactorily. Each composition raw material and molding condition are described in Table 2.

The dental pulp in Examples was also produced by preliminarily molding and inserting it into the dental pulp portion.

(Method for Preparing Artificial Tooth 4-1)

Figure 8:
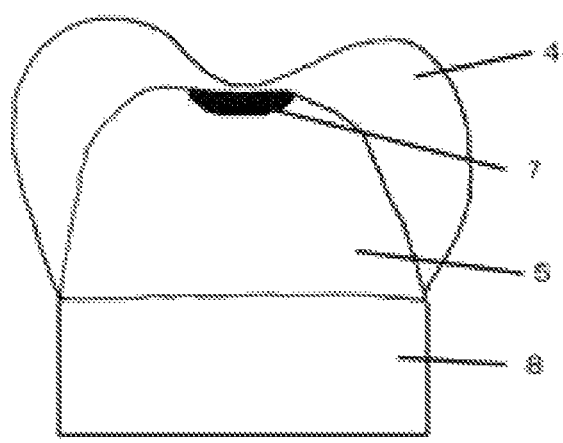
FIG. 8 is a view of tooth morphology obtained by powder compression molding in three layers of an enamel tooth, a dentin tooth, and a dental caries (third layer).

A plurality of convex molds were used in the same manner as in "(Method for Preparing Artificial Tooth 3-1)" to prepare an artificial tooth having the dental caries shown in FIG. 8.

Ten artificial teeth were respectively molded from the compositions and under the molding conditions shown in Examples 32 to 41 by the above method "(Method for Preparing Artificial Tooth 4-1)". It was verified that the artificial teeth could be molded satisfactorily. Each composition raw material and molding condition are described in Table 2.

TABLE 1

| Composition name | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Xylitol | 100 | | | | 50 | | 10 | 95 | 90 | 80 | 29 | | | 29 | | |
| Maltitol | | 100 | | | 50 | | | | | | | | 67 | | 67 | |
| Starch | | | 100 | | | 50 | 40 | | | | | | | | | |
| Powdered milk | | | | 100 | | 50 | 50 | | | | | | 49 | | | 49 |
| Silica powder (30 μm) | | | | | | | | 5 | 10 | 20 | 70 | 30 | 50 | 70 | 30 | 50 |
| Carbon black | | | | | | | | | | | 1 | 1 | 1 | | | |
| Red pigment (iron red) | | | | | | | | | | | | | | 1 | 1 | 1 |

(% by mass)

TABLE 2

|  | Example 1 | Example 2 | Example 3 | Example 4 | Example 5 | Example 6 | Example 7 | Example 8 | Example 9 | Example 10 |
|---|---|---|---|---|---|---|---|---|---|---|
| Enamel composition | 1 | 2 | 3 | 4 | 5 | 6 | 7 | 8 | 9 | 10 |
| Dentin/root composition | 1 | 2 | 3 | 4 | 5 | 6 | 7 | 8 | 9 | 10 |
| Enamel molding pressure (MPa) | 20 | 90 | 20 | 80 | 40 | 60 | 60 | 60 | 60 | 60 |
| Dentin/root molding pressure (MPa) | 20 | 90 | 20 | 80 | 40 | 60 | 60 | 60 | 60 | 60 |
| Moldability | Satisfactory | Satisfactory | Satisfactory | Satisfactory | Satisfactory | Satisfactory | Satisfactory | Satisfactory | Satisfactory | Satisfactory |

|  | Example 11 | Example 12 | Example 13 | Example 14 | Example 15 | Example 16 | Example 17 | Example 18 | Example 19 |
|---|---|---|---|---|---|---|---|---|---|
| Enamel composition | 1 | 1 | 1 | 2 | 2 | 2 | 2 | 2 | 2 |
| Dentin/root composition | 1 | 1 | 1 | 3 | 3 | 3 | 9 | 10 | 10 |
| Enamel molding pressure (MPa) | 60 | 80 | 90 | 60 | 80 | 90 | 60 | 80 | 90 |
| Dentin/root molding pressure (MPa) | 10 | 50 | 70 | 10 | 50 | 70 | 10 | 50 | 70 |
| Moldability | Satisfactory | Satisfactory | Satisfactory | Satisfactory | Satisfactory | Satisfactory | Satisfactory | Satisfactory | Satisfactory |

|  | Example 20 | Example 21 | Example 22 | Example 23 | Example 24 | Example 25 | Example 26 | Example 27 | Example 28 | Example 29 |
|---|---|---|---|---|---|---|---|---|---|---|
| Enamel composition | 1 | 1 | 1 | 1 | 1 | 1 | 3 | 4 | 1 | 1 |

TABLE 2-continued

| | | | | | | | | | | |
|---|---|---|---|---|---|---|---|---|---|---|
| Dentin/root composition | 1 | 1 | 1 | 1 | 1 | 1 | 3 | 4 | 4 | 10 |
| Dental pulp composition | 14 | 15 | 16 | 14 | 15 | 16 | 14 | 15 | 16 | 14 |
| Enamel molding pressure (MPa) | 60 | 60 | 60 | 60 | 60 | 60 | 60 | 60 | 60 | 60 |
| Dentin/root molding pressure (MPa) | 60 | 60 | 60 | 20 | 20 | 20 | 20 | 20 | 20 | 20 |
| Dental pulp molding pressure (MPa) | 60 | 60 | 60 | 10 | 10 | 10 | 10 | 10 | 10 | 10 |
| Moldability | Satisfactory | Satisfactory | Satisfactory | Satisfactory | Satisfactory | Satisfactory | Satisfactory | Satisfactory | Satisfactory | Satisfactory |

| | Example 30 | Example 31 |
|---|---|---|
| Enamel composition | 1 | 1 |
| Dentin/root composition | 1 | 1 |
| Dental pulp composition | Resin | Silicone |
| Enamel molding pressure (MPa) | 60 | 60 |
| Dentin/root molding pressure (MPa) | 20 | 20 |
| Dental pulp molding pressure (MPa) | 10 | 10 |
| Moldability | Satisfactory | Satisfactory |

| | Example 32 | Example 33 | Example 34 | Example 35 | Example 36 | Example 37 | Example 38 | Example 39 | Example 40 | Example 41 |
|---|---|---|---|---|---|---|---|---|---|---|
| Enamel composition | 1 | 1 | 1 | 1 | 1 | 1 | 3 | 4 | 1 | 1 |
| Dentin/root composition | 1 | 1 | 1 | 1 | 1 | 1 | 3 | 4 | 4 | 10 |
| Dental caries composition | 11 | 12 | 13 | 11 | 12 | 13 | 11 | 12 | 13 | 11 |
| Enamel molding pressure (MPa) | 60 | 60 | 60 | 60 | 60 | 60 | 60 | 60 | 60 | 60 |
| Dentin/root molding pressure (MPa) | 60 | 60 | 60 | 20 | 20 | 20 | 20 | 20 | 20 | 20 |
| Dental caries molding pressure (MPa) | 60 | 60 | 60 | 10 | 10 | 10 | 10 | 10 | 10 | 10 |
| Moldability | Satisfactory | Satisfactory | Satisfactory | Satisfactory | Satisfactory | Satisfactory | Satisfactory | Satisfactory | Satisfactory | Satisfactory |

The following effects were confirmed from each Example.

The same composition is used for the composition of the enamel portion, the composition of the dentin portion, and the composition of the root portion. Thereby, the control of raw materials is easy and preferred.

Cuttability was able to be changed by changing the molding pressure of the enamel portion and the dentin portion while using the same raw materials. It is important to obtain a cutting feeling of the enamel portion and the dentin portion. When five dentists evaluated the cuttability of artificial teeth prepared in Examples 1 to 19, the result was that the artificial teeth of Examples 11 to 19 were similar to a natural teeth.

By using silica powder in the composition, a cutting feeling became flexible, and the same cutting feeling as that of the dentin portion was able to be obtained.

Since the dental pulp portion is colored, the dental pulp exposure is easily found.

The dental pulp exposure can be felt by using a resin and silicone for the dental pulp portion.

INDUSTRIAL APPLICABILITY

The present invention provides a tooth for a jaw tooth model for a dental college student to practice cavity preparation and abutment tooth preparation which are therapeutic actions, and the tooth can be utilized for industry.

What is claimed is:

1. A compression molded tooth used for practicing dental cutting treatment consisting of a compression molded article of a composition consisting of a powder or powders of saccharide, polysaccharide, protein, and/or glycoprotein each having a particle size of 1 to 100 μm.

2. The compression molded tooth according to claim 1, wherein the tooth has portions where the numbers of compression molding cycles are different.

3. The compression molded tooth according to claim 1, wherein the tooth comprises a first portion constituting an enamel tooth portion and a second portion constituting a dentin tooth portion, wherein the number of compression molding cycles for the first portion is larger than the number of compression molding cycles for the second portion.

4. The compression molded tooth according to claim 1, wherein the tooth has a third portion different from the first portion and the second portion therein.

5. The compression molded tooth according to claim 4, wherein the third portion constitutes a dental caries portion, a dental pulp portion, and/or a cutting target portion.

6. A method for producing a compression molded tooth according to claim 1 comprising: molding a crown side using a concave mold; and molding a root side using a convex mold.

7. The method for producing a compression molded tooth according to claim 6, wherein an enamel tooth portion closer to an occlusal surface is molded using a first convex mold, and then a dentin tooth portion is molded using a second convex mold.

8. The method for producing a compression molded tooth according to claim 7, wherein molding pressure for the first convex mold is 20 to 100 MPa; molding pressure for the second convex mold is 5 to 85 MPa; and the molding pressure for the second convex mold is lower by 15 MPa or more as compared with the molding pressure for the first convex mold.

\* \* \* \* \*